(12) United States Patent
Gillies et al.

(10) Patent No.: US 9,192,022 B2
(45) Date of Patent: Nov. 17, 2015

(54) LIGHT CONTROL SYSTEM FOR USE WITHIN A HOSPITAL ENVIRONMENT

(75) Inventors: Murray Fulton Gillies, Eindhoven (NL); Tim Johannes Willem Tijs, Stramproy (NL); Juergen Vogt, Kamen (DE); Harold Agnes Wilhelmus Schmeitz, Eindhoven (NL); Ewa Aurelia Miendlarzewska, Gaillard (FR); Gijs Antonius Franciscus Van Elswijk, Eindhoven (NL); Marek Janusz Bartula, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 18 days.

(21) Appl. No.: 13/982,556

(22) PCT Filed: Jan. 27, 2012

(86) PCT No.: PCT/IB2012/050383
§ 371 (c)(1),
(2), (4) Date: Mar. 12, 2014

(87) PCT Pub. No.: WO2012/104758
PCT Pub. Date: Aug. 9, 2012

(65) Prior Publication Data
US 2014/0232298 A1 Aug. 21, 2014

(30) Foreign Application Priority Data
Feb. 1, 2011 (EP) .................................. 11152935

(51) Int. Cl.
*H05B 37/02* (2006.01)
*A61B 6/03* (2006.01)
(52) U.S. Cl.
CPC ............ *H05B 37/02* (2013.01); *H05B 37/0227* (2013.01); *A61B 6/037* (2013.01)

(58) Field of Classification Search
USPC ......... 315/149, 152, 158, 291, 307, 308, 312, 315/360
See application file for complete search history.

(56) References Cited

U.S. PATENT DOCUMENTS

| 5,093,769 | A | 3/1992 | Luntsford | |
|---|---|---|---|---|
| 2004/0052076 | A1 | 3/2004 | Mueller et al. | |
| 2005/0281030 | A1* | 12/2005 | Leong et al. | 362/234 |
| 2006/0010799 | A1 | 1/2006 | Bohm et al. | |
| 2008/0265799 | A1* | 10/2008 | Sibert | 315/292 |
| 2009/0212719 | A1 | 8/2009 | Wedel | |
| 2010/0060726 | A1 | 3/2010 | Kryger Nielsen et al. | |
| 2010/0141153 | A1* | 6/2010 | Recker et al. | 315/149 |
| 2010/0315023 | A1 | 12/2010 | Pesson et al. | |

FOREIGN PATENT DOCUMENTS

| WO | WO2006038169 | 4/2006 |
|---|---|---|
| WO | WO2008062384 | 5/2008 |

* cited by examiner

*Primary Examiner* — Tung X Le

(57) ABSTRACT

The invention relates to a control system (100) for an ambient light environment in a room in a hospital environment. The control system is configured to time and synchronize light effects of the ambient light environment (170, 190) in response to sensor signals (111-113) from patient location sensors (121) or other sensors (122,123) for detecting if a clinical instrument is activated, moved or taken into use or for detecting heart rate. Light effects may be used by the clinical personnel to improve quality and speed of the examination and to create a calming atmosphere for the patient. However, different light effects are required at different times and for different durations. Therefore, timing of the light effects relative to sensor signals may improve workflow and patient comfort.

10 Claims, 4 Drawing Sheets

LIGHT CONTROL SYSTEM FOR USE WITHIN A HOSPITAL ENVIRONMENT

CROSS-REFERENCE TO PRIOR APPLICATIONS

This application is the U.S. National Phase application under 35 U.S.C. §371 of International Application Ser. No. PCT/IB2012/050383, filed on Jan. 27, 2012, which claims the benefit of European Application Ser. No. 11152935.0, filed on Feb. 1, 2011. These applications are hereby incorporated by reference herein.

FIELD OF THE INVENTION

The invention relates to a control system for controlling lighting and visual effects, in particular to such a system for use within a hospital environment.

BACKGROUND OF THE INVENTION

The workflow during an uptake period immediately before a PET (positron emission tomography) scan is very important for the quality of the scan. During this uptake period the patient is injected with a radioactively labeled sugar, often FDG, and subsequently scanned with either a standalone PET scanner or a combination of PET with either CT or MR for anatomical information. A number of steps have to be performed by the clinical personnel several of which require a high level of patient compliance. There is a need to make this workflow run more smoothly.

Patient relaxation is of crucial importance in the time period immediately before and after the injection. If the patient is stressed in this period then the uptake will not be successful with FDG or radioactively labeled sugar being excessively consumed by overly stressed muscles and brain activity. Patients often get anxious during this uptake period due to the fact that they are in unfamiliar surroundings, are unsure about the examination and may have previous negative associations with clinical devices and or environments. Accordingly, there is a need to improving patient comfort and reducing anxiety before and during the examination.

Furthermore, patients are often of advanced age and have narrow veins that are difficult to locate. The injection is therefore often a difficult procedure which may increase patient anxiety and may prolong the examination. Thus, there is a need to improve the injection process.

US 2010060726 discloses a medical surgery or examination room and a method for illuminating such a room, wherein a substantial part of the room or the entire room is illuminated with colored lighting different from white lighting in order to achieve beneficial psychological effects or, primarily, to improve working conditions. For example, green light may be provided behind the monitors used by a surgeon during operation and red light in a zone behind a surgeon during operation or examination. The lighting may be controlled by a computer with a touch screen interface.

Whereas US 2010060726 discloses a lighting system for use within a hospital environment, the inventors of the present invention has appreciated that an improved lighting control system is of benefit, and has in consequence devised the present invention.

SUMMARY OF THE INVENTION

It would be advantageous to achieve improvements of light control systems for controlling lighting within a hospital environment. It may be seen as an object of the present invention to provide a method and a system that solves the above mentioned problems relating to the examination workflow, patient anxiety, difficulty in locating veins or other problems of the prior art.

To better address one or more of these concerns, in a first aspect of the invention a light control system for controlling lighting in a room within a hospital environment is presented where the control system comprises a controller having an input for receiving a first sensor signal indicative of a location of a patient or a clinical instrument or device, and an output for outputting at least a first control signal to a controllable light, where the controller is configured to generate the first control signal in response to the first sensor signal, a time-scheduler configured to delay the outputting or generation of the first control signal, where the delay is set relative to a time of receipt of the first sensor signal.

The first sensor signal could be generated by a pressure sensor placed so that when a patient sits or lies on a bed then a signal indicative of the location of the patient is generated. Other patient location sensors may be used such as a video surveillance system that determines the location of a patient. A controllable light could be a light, e.g. a LED light, capable of being controlled via a control signal to emit light of different colors and intensities.

The time-scheduler is able to delay the generation or outputting of the first control signal. For example, the time-scheduler may be configured so that a sequence of different light effects (i.e. different colors and intensities) are generated in response to the first input signal where the time-scheduler controls the delay between the first input signal and the light effects, possibly the duration of each light effect, and possibly gradual changes of light effects. In this way, the controllable light may be controlled so that firstly light which reduces patient anxiety is generated, secondly light which improves visibility of veins is generated so that the injection with radioactively labeled sugar can be performed accurately and without discomfort, and thirdly light which reduces patient anxiety and calms the patient is generated to ensure that the radioactively labeled sugar is only taken up by the tumor and not by stress induced muscle or brain activity. Thus, the timing of the generation of the control signal or different control signals may be beneficially for one or more of reducing patient anxiety, improving vein visibility and improving the workflow of the examination by tailoring the lighting settings to the specific stages of the examination procedure.

The amount of delay between receipt of the first input signal to outputting or generating the first control signal may be stored in a storage medium or unit being accessible by the control system for retrieval of suitable delay values.

In an embodiment the controller is configured for generating a time dependent first control signal, where a value of the first control signal changes over time so as to enable a gradual change of a color or an intensity of the controllable light. Accordingly, when the controllable light is controllable to change color or intensity in response to its input signal value, changing the analogue or digital value of the control signal from the controller enables the color and/or intensity to be gradually adjusted. In this way seamless transitions between different light effects may be achieved as well as gradual variations in light color and intensity in order to increase or reduce the calming effect of the lighting.

In an embodiment the controller is configured for generating a second control signal for controlling a visual stimulation device, where the controller is configured for generating the second control signal in response to the first sensor signal and/or in response to a second sensor signal, where the first signal is indicative of a location of a patient and the second signal is indicative of a movement or a location of a clinical instrument or device, and where the time-scheduler is configured to time outputting of the second control signal relative to receipt of the first input signal or the second input signal.

A visual stimulation device may be a monitor or a projector capable of displaying images. Accordingly, the controller may be able to output different images via the second control signal to the stimulation device for displaying images which provides e.g. a calming effect to the patient. The generation or outputting of the second control signal may be timed by the time-scheduler in response to receipt of the same first sensor signal as in the first aspect being indicative of a location of a patient or in response to a different sensor signal being indicative of a movement or a location of a clinical instrument or device.

Accordingly, the controller may have inputs for receiving first and second input signals and respective outputs for making first and second control signals available for a light and a visual stimulation device, respectively.

In an embodiment the controller has an input for receiving a second sensor signal indicative of a movement or a location of an intravenous needle, where the controller is configured to generate the first control signal in response to the first or the second sensor signal.

The second sensor signal may be provided to the controller via the same input which is connected to receive the first sensor signal or via a separate input. The first control signal may be generated in response to the first or the second sensor signal, i.e. the first control signal is generated both when the first sensor signal is received and when the second sensor signal is received.

The second sensor signal may be generated by an RF tag situated within a lead box storing the intravenous needle containing the radioactive fluid. Thus, when the needle with the attached RF tag is removed from the lead box or when the box is opened, the RF tag is detectable and the second sensor signal can be generated. Alternatively, the second sensor signal may be generated by a radioactive sensitive detector which is able to detect when the needle is removed from the lead box.

In an embodiment the control system comprises a storage including a number of selectable control schemes, where each control scheme defines the delay of outputting the first control signal relative to the first sensor signal and/or a time dependence of a change of a value of the first control signal, and where each control scheme is selectable via a user input device.

For example, a first control scheme may be configured to control the light in a way which is suitable for the uptake period before subsequent brain scans and a second control scheme may be configured for to control the light in a way which is suitable for breast scans. The brain scan control scheme may exclude high light intensities and rapid color changes as to reduce neurological stimulation as much as possible. Thus, the clinical personnel is able to select a control scheme which is suited for a particular examination.

In an embodiment the first sensor signal is generated by a pressure sensor capable of detecting the presence of a patient in a bed or a sensor capable of detecting the presence of a radioactively labeled fluid to be injected into a vein of the patient.

Thus, the first sensor may be an RF type sensor or a radiation sensor capable of sensing when the lead box storing the intravenous needle containing radioactive fluid is opened or when the needle is removed from the box.

In an embodiment the controller further comprises an input for receiving a signal indicative of the heart rate of the patient, where the controller is configured for generating the second control signal for controlling the visual stimulation device in dependence of the signal indicative of the heart rate of the patient. Accordingly, by controlling the visual stimulation device in dependence of the heart rate, the visual stimulation device may be used to effectively affect the heart rate of the patient, for example by displaying calming images if a too high hart rate is detected. Alternatively or additionally, the controller may be configured for generating the time dependence of the first control signal in dependence of the detected heart rate, e.g. for ensuring slow changes in intensity or color of the controllable light if a too high heart rate is detected. Alternatively the breathing rate may be determined by a device and the controller. The controller is configured to first register the breathing rate and feedback this to the patient in the form of a breathing exercise, e.g. changing the light parameters with the breathing frequency. The rate is then slowly decreased to approximately 6 times per minute. This breathing rate is optimal for paced breathing and induction of a relaxed state in the patient.

In an embodiment the controller is configured for generating a third control signal in dependence of the first input signal for controlling a computer controlled pointing device capable of locating the position of veins in a patient and pointing at a vein location suitable for injection of a fluid, where the time-scheduler is configured to delay outputting the third control signal relative to the time of receipt of the first sensor signal. Thus, the receipt of the first sensor signal triggers a delayed generation of the third control signal for starting detection of a vein location and pointing at a vein location suitable for injection of the radioactive fluid. The detection of vein locations may be performed by analyzing images of the arm of a patient and the pointing towards a suitable vein location may be performed by a laser pointing device. Thus, the third control signal may be generated in response an input signal indicative of a location of a patient or a clinical instrument or device.

A second aspect of the invention relates to a light unit for use within a hospital environment, where the unit comprises
   a light control system according to the first aspect, and
   a monitor for displaying images and/or a controllable light.

Additionally, the unit may comprise an audio device for generating music or other sounds.

The control system and one or more of the monitor, the light and the audio device may be integrated into a single unit which may be mounted onto a wall. The light unit may also comprise any sensor for generating any of the first, second and third input signals.

A third aspect of the invention relates to a method for controlling lighting in a room within a hospital environment, where the method comprises,
   receiving a first sensor signal indicative of a location of a patient or a clinical instrument or device,
   generating a first control signal to a controllable light by use of a controller configured to generate the first control signal in response to receipt of the first sensor signal,
   where the generation or outputting of the first control signal is delayed relative to a time of receipt of the first sensor signal, where the delay is controlled by a time-scheduler.

In general the various aspects of the invention may be combined and coupled in any way possible within the scope of the invention. These and other aspects, features and/or advantages of the invention will be apparent from and elucidated with reference to the embodiments described hereinafter.

In summary the invention relates to a control system for an ambient light environment in a room in a hospital environment. The control system is configured to time and synchronize light effects of the ambient light environment in response to sensor signals from patient location sensors or other sensors for detecting if a clinical instrument is activated, moved or taken into use or for detecting heart rate. Light effects may be used by the clinical personnel to improve quality and speed of the examination and to create a calming atmosphere for the patient. However, different light effects are required at different times and for different durations. Therefore, timing of the light effects relative to sensor signals may improve workflow and patient comfort.

BRIEF DESCRIPTION OF THE DRAWINGS

Embodiments of the invention will be described, by way of example only, with reference to the drawings, in which.

DETAILED DESCRIPTION OF EMBODIMENTS

Imaging of tumors via PET has become an important part of diagnosing and prognosing oncology patients. PET imaging involves injecting patients with a radioactively labeled sugar, FDG, which is metabolized by the tumor at a faster rate than other muscles and organs. This highlights the tumor location and allows the tumor mass to be assessed by the clinician. To improve this assessment, PET images are often combined with either a CT or MR scan to allow anatomical information to be fused together with the PET contrast.

Since the uptake of the FDG tracer by the human body is essentially non-specific, the tracer will gather at any location in the body that utilizes sugar. The patient is therefore required to remain as calm as possible (both mentally and physically) during the uptake period. This minimizes the sugar being consumed by non-tumor related features.

Avoiding anxiety, however, may be very challenging for a patient since the patient is about to receive a medical prognosis regarding a possibly life-threatening disease, since the patient has to be injected with a radioactive material, since the patient will be inserted into a scanner which may cause claustrophobia feelings, and since the patient is located in an unfamiliar and very clinical environment.

Since the patient has to remain calm at least during part of the examination, it is often not possible to distract the patient by use of distractive means such as a TV during the full uptake period of the radioactive fluid.

In a typical PET examination the patient is initially introduced to the uptake room where the radioactive fluid will be injected, then the patient is instructed to remain still, quiet and calm for a period up to the injection, then the injection is given, and then the patient is again instructed to remain calm during the uptake until the scanning can be performed.

Figure 1:
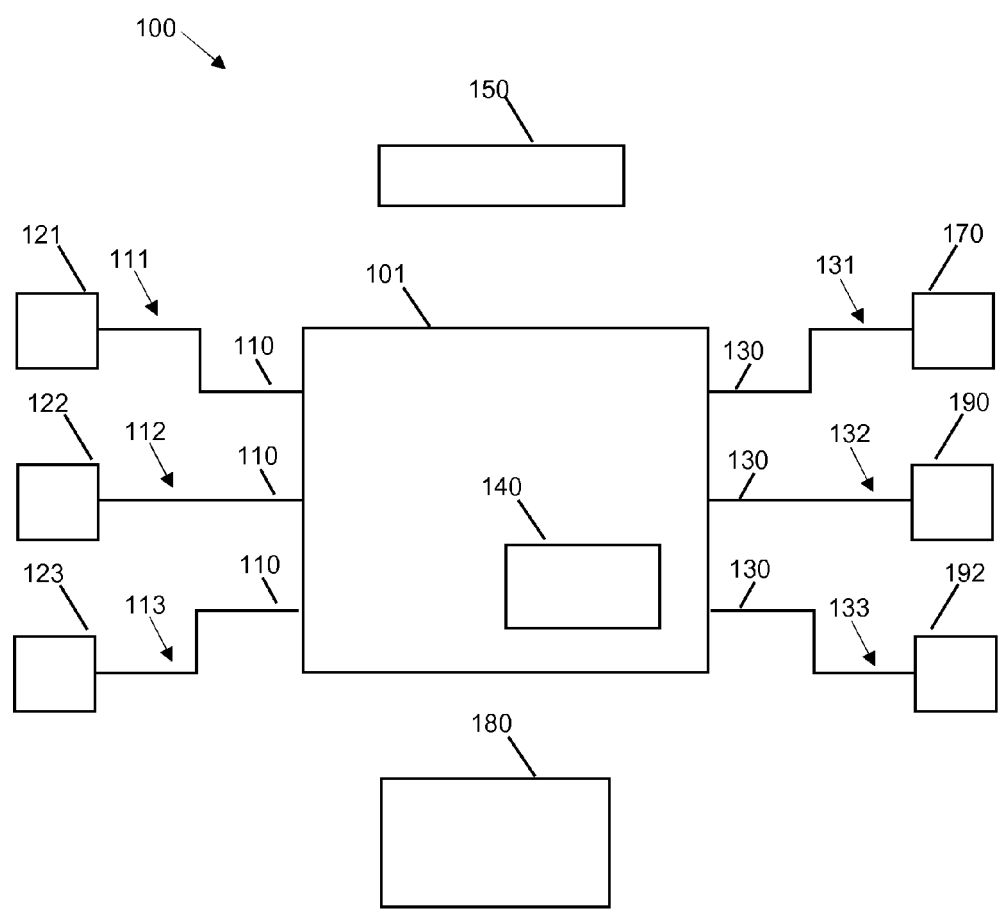
FIG. 1 shows a control system 101 for controlling ambient light in a hospital room.

FIG. 1 shows a light control system 100 for controlling lighting in a room within a hospital environment in response to input signals 111-113 from sensors 121-123. The lighting may include controllable lights 170 and possibly visual stimulation devices 190 such as TV monitors. The control system includes a controller 101 having an input 110 for receiving one or more sensor signals indicative of a location of a patient or a clinical instrument or device. The control system may have separate inputs 110 for receiving first, second and third sensor signals 111-113, respectively. The sensor signals are generated by sensors 121-123 such as sensors for detecting a location of a patient and for detecting position, removal, motion or use of clinical instrument or device. Location of a patient may be detected by a pressure sensor located in the mattras of a bed or a chair, an optical sensor or with camera and image analysis software. Detection of the location of clinical instruments such as intravenous needles and hypodermic needles and devices such a hand held scanners may be enabled by acceleration sensors or RF tags connected to the instrument or device. As a special example, an intravenous or hypodermic needle containing a radioactively labeled fluid is stored in a lead box to avoid radioactive emissions. The opening of the lead box or removal of the needle from the box can beneficially be detected by exploiting that the lead box stops or reduces radioactive and electromagnetic emissions. Accordingly, a radiation sensor located outside the box can be used to detect the opening of the box. Similarly, it is possible to detect if the box is open by an RF tag attached to the inside of the box. Opening the lid of the box allows the electromagnetic sense waves to reach the RF tag and thus generate a presence, or box open, signal.

The room lighting is controlled by one or more control signals provided via one or more outputs 130. The controller generates the control signals in response to one or more of the sensor signals, e.g. in response to the first sensor signal 111. A time-scheduler is configured to delay or time the outputting of the one or more control signals. The delay is set relative to the time of receipt of one of the sensor signals, e.g. the first sensor signal 111.

The time-scheduler 180 may be a separate component or integrated with the controller 101. The controller 101 and the time-scheduler 180 may be implemented as analogue or digital electronic circuits, as a computer program stored on a tangible media, e.g. a CD, designed to be executed by a processor or a computer, or they may be implemented as a combination of electronic circuits and a computer program. The inputs 110 and outputs 130 may be configured as input and output terminals of an electronic circuit which possibly is connectable to a computer, or by terminals of a computer.

Figure 2:
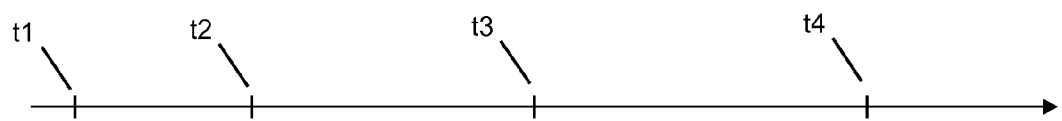
FIG. 2 illustrates relationship between input signals and delayed generation of control signals.

FIG. 2 provides an example of the function of the light control system 100. At time t1 a patient lies on a bed and a first sensor signal is generated from the bed sensor. In response to the first sensor signal 111, the controller generates a first control signal 131 for controlling the controllable light 170 into a first state to provide a comfortable light intensity and color. The first state may be invoked during the first period from t1 to t2. During the first period the value of the first control signal 131 may change over time so as to generate a gradual change of the color or the intensity of the controllable light. The gradual change may provide seamless transitions between different states of the controllable light or provide more interesting, yet calming light effects.

Alternatively or additionally, during the first period from t1 to t2, a second control signal 132 may be generated in response to the first input signal 111 for controlling a monitor 190 for displaying images or videos, where the time-scheduler is configured to time outputting or generation of the second control signal 132 relative to receipt of the first input signal 111.

At time t2, in response to the first sensor signal 111 the controller generates a first control signal 131 for controlling the controllable light into a second state to provide a green light which helps the clinical personnel to locate veins of the patient. The green light is maintained for a preset period up to time t3 or until the clinical personnel manually provides an input to the controller 101 via a user input device to force the controller to end this second light state.

Alternatively, the generation of the first control signal 131 at time t2 for controlling the controllable light into a second state to provide a green light may be done in response to a second sensor signal 112 indicative of a movement or a location of a clinical instrument. The second sensor signal may be generated when the intravenous or hypodermic needle containing radioactively labeled fluid is removed from its lead box, e.g. by a radiation sensor. The radiation sensor may be located near the place where the injection is to be performed so that light changes to green light just before the injection.

At time t3, the injection is completed and the patient should remain calm for a third period up to time t4. During the third period the light 170 or the monitor 190 is controlled to generate light effects or images which have a calming effect on the patient. The first or second control signal for controlling the controllable light 170 or the controllable monitor 190 into a third state during the period from t3 to t4 may be generated in response to the first input signal 111 or preferably in response to the second input signal 112 generated in response to the movement of a clinical instrument.

It is understood that different values of the first or second control signals 131,132 invoke different states of the light 170 or the monitor 190, i.e. different intensity and color states or images.

It is also understood that the first sensor may be a sensor capable of detecting the location of a patient, the presence of a patient in a bed, detecting the location or movement of clinical instruments, detecting the presence of a radioactively labeled fluid, or other sensors capable of detecting various changes in the environment within a room of a clinical environment.

The time-scheduler generates the required delays necessary to obtain the correct timing for maintaining a given light state and changing between light states.

In an embodiment the light controller 101 comprises an input for receiving a third input signal 113 indicative of the heart rate of the patient. A sensor 123 for detecting the heart rate may be conventional finger or breast pulsation detectors or a camera with an associated image analysis processor for detecting variations in blood flow. The third input signal may also be the breathing rate of the patient (sense either by a band or camera) and which allows the anxiety level of the patient to be assessed. The first or second control signal for controlling lights 170 or a monitor 190 may be generated in response to the third input signal 113 so that colors and light intensity or images from the monitor can be adjusted in response to the heart rate of the patient. For example, if the heart rate starts increasing the light intensity may be reduced or more relaxing images or music may be reproduced.

In an embodiment the controller is configured for generating a third control signal 133 for controlling a computer controlled pointing device 192 capable of detecting location of veins of a patient and pointing at a vein location suitable for injection of a fluid. The third control signal may be generated in response to the first sensor signal in which case the time-scheduler delays outputting or generation of the third control signal relative to receipt of the first control signal. Alternatively, the third control signal 133 may be generated in response to the second sensor signal 112 indicative e.g. of the removal of an instrument for injecting radioactive labeled fluid.

The control system 100 may comprise a storage 140 which may be integrated with the controller 101 where the storage is for storing a number of selectable control schemes. Each control scheme defines how any one or more of the first, second and third control signals 131-133 will be generated in response to any of the first, second or third input signals 111-113. Thus, each control scheme defines which of the first, second and third control signals 131-133 should be generated in response to any of the first, second or third input signals 111-113, and defines the delay from receipt of any of first, second or third input signals 111-113 to generation or outputting of any of the first, second or third control signals 131-133. The delay may be a time from zero up to several minutes and hours. Furthermore, the control scheme may define if and how values of the control signals should vary over time and the duration of any state of the light 170 or the monitor 190.

Each of the control schemes may be selectable by a user of the control system 100 via a user input device 150 such as a touch pad or a keyboard. Accordingly, depending on the type of examination to be performed or the sex or age of the patient the most suitable control scheme can be selected. For example, for a brain scan examination a control scheme which excludes very bright light and rapid color changes may be selectable so as to reduce neurological stimulation as much as possible, whereas a for breast scan examination more stimulating light effects and images may be defined by a control scheme suitable for this type of examinations.

Figure 3:
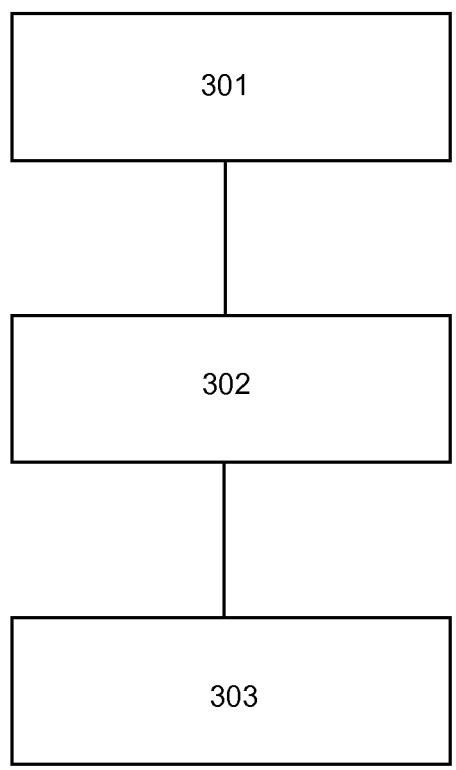
FIG. 3 illustrates a method according to the invention.

FIG. 3 illustrates a method according to an embodiment of the invention which comprises the following steps:

Step 301: Receiving a first sensor signal 111 indicative of a location of a patient or a clinical instrument or device.

Step 302: Generating a first control signal 131 to a controllable light 170 by use of a controller 101 configured to generate the first control signal in response to receipt of the first sensor signal.

Step 303: Generating a delay between the time of receipt of the first sensor signal and the generation or outputting of the first control signal by use of a time-scheduler 180.

It is understood that step 303 is not necessarily performed after generation of the control signal, but may be performed when or after the first sensor signal or other sensor signals is received and before or at the time of generation of the control signal. Thus, the control signal may be generated when the input signal is received, but the outputting of the generated control signal may be delayed. Alternatively, when the input signal is received a delay may have to lapse before the control signal is generated.

Figure 4:
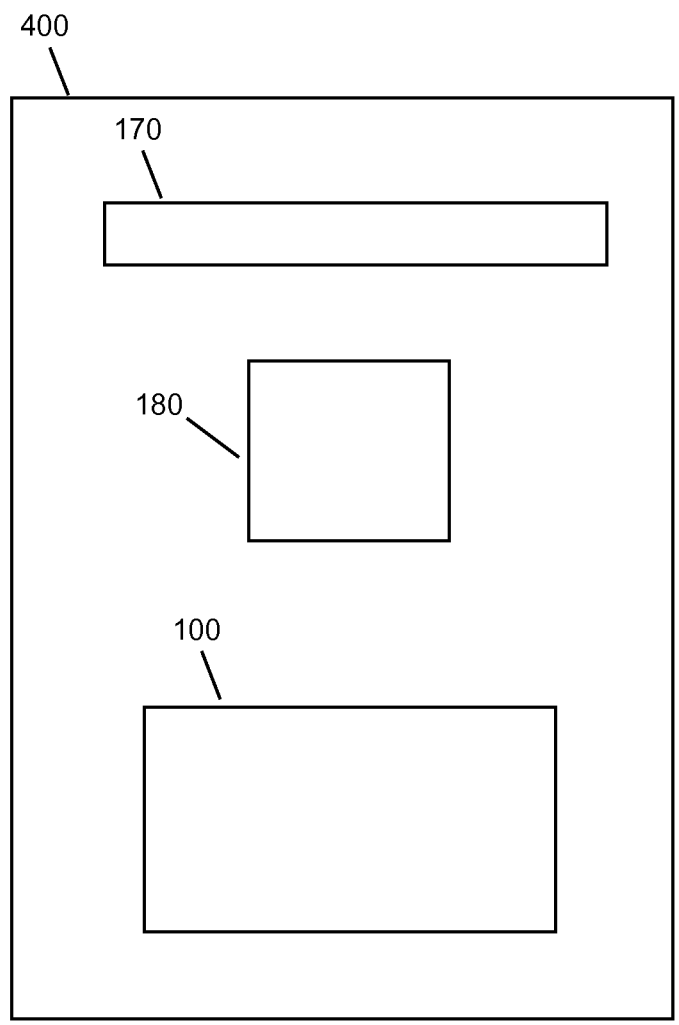
FIG. 4 shows an ambient light unit 400 comprising the control system 100 and lights 170.

FIG. 4 shows an ambient light unit 400 which comprises the light control system 100 and a monitor 190 for displaying images and/or a controllable light 170. The unit may be fixedly mounted in the hospital room, e.g. on a wall, so that the monitor 190 is visible for the patient lying on a bed and facing the ceiling. One or more lights 170 may be integrated in the unit 400 for background illumination of the room and for providing light directed towards the patient for situations where the patient is examined or where an injection is performed. The light unit 400 may be placed in the uptake room where the radioactive labeled fluid is injected. The scanning may be performed in the same room or in an adjacent room. Also a recovery room may be used in connection with the examination which is used for the patient to recover after the examination. The recovery room may have a separate light unit 400 installed.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage.

A single processor or other unit may fulfill one or more functions of several items recited in the claims, e.g. the generation and timing of the generation or outputting of the control signals in response to input signals. A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A light control system for controlling lighting in a room within a hospital environment, the control system comprising;
    a controller having an input for receiving a first sensor signal indicative of at least one of a location and a movement of a clinical instrument, and an output for outputting at least a first control signal to a controllable light,
    wherein the controller is configured to generate the first control signal in response to the first sensor signal; and
    a time-scheduler configured to at least one of delay the outputting and the generation of the first control signal,
        wherein the delay is set relative to a time of receipt of the first sensor signal.

2. A light control system according to claim 1,
    wherein the first control signal is time dependent; and
    wherein a value of the first control signal changes over time so as to enable a gradual change of at least one of a color and an intensity of the controllable light.

3. A light control system according to claim 1,
    wherein the controller has an input for receiving a second sensor signal indicative of at least one of one of a movement and a location of an intravenous or hypodermic needle; and
    and wherein the controller is configured to generate the first control signal in response to at least one of the first and the second sensor signal.

4. A light control system according to claim 1,
    wherein the control system includes a storage unit including a number of selectable control schemes;
    wherein each control scheme defines the delay of at least one of the generation and the outputting the first control signal relative to at least one of the first sensor signal and a time dependence of a change of a value of the first control signal; and
    wherein each control scheme is selectable via a user input device.

5. A light control system according to claim 1, wherein the first sensor signal is generated by a sensor capable of detecting the presence of a radioactively labeled fluid to be injected into a vein of the patient.

6. A light control system according to claim 1,
    wherein the controller is configured for generating a third control signal in dependence of the first input signal for controlling a computer controlled pointing device capable of detecting location of veins of a patient and pointing at a vein location suitable for injection of a fluid; and
    wherein the time-scheduler is configured to delay outputting the third control signal relative to the time of receipt of the first sensor signal.

7. A light control unit for a hospital environment, the unit comprising:
    a light control system according to claim 1; and
    a monitor in communication with the light control system for displaying images and/or the controllable light.

8. A method for controlling lighting in a room within a hospital environment, the method comprising;
    receiving a first sensor signal indicative of a location of at least one of patient, a clinical instrument and a clinical device; and
    generating a first control signal to a controllable light by use of a controller configured to generate the first control signal in response to receipt of the first sensor signal,
    wherein the generation or outputting of the first control signal is delayed relative to a time of receipt of the first sensor signal, and
    wherein the delay is controlled by a time-scheduler.

9. A light control system for controlling lighting in a room within a hospital environment, the control system comprising;
    a controller having an output for receiving a first sensor signal indicative of a location of a patient and an output for outputting at least a first control signal to a controllable light,
        wherein the controller is configured to generate the first control signal in response to the first sensor signal; and
    a time-scheduler configured to at least one of delay in outputting or a generation of the first control signal,
    wherein the delay is set relative to a time of receipt of the first sensor signal,
    wherein the controller is configured for generating a second control signal for controlling a visual stimulation device,
    wherein the controller is configured for generating the second control signal in response to at least one of the first sensor signal and a second sensor signal,
    wherein the second signal is indicative of at least one of a movement and a location of a clinical instrument, and
    wherein the time-scheduler is configured to at least one of a delay in outputting or a generation of the second control signal relative to the time of receipt of at least one of the first input signal and the second input signal.

10. A light control system according to claim 9,
    wherein the controller includes an input for receiving a signal indicative of at least one of a heart rate and a breathing rate of the patient; and
    wherein the controller is configured for generating the second control signal in dependence of the signal indicative of at least one of the heart rate and the breathing rate of the patient.

* * * * *